United States Patent
Li

(10) Patent No.: US 7,344,662 B2
(45) Date of Patent: Mar. 18, 2008

(54) REVERSE SYNTHETIC METHODS FOR MAKING ORGANIC NON-LINEAR OPTICAL MATERIALS

(75) Inventor: Sheng Li, Vista, CA (US)

(73) Assignee: Nitto Denko Corporation, Osaka (JP)

( * ) Notice: Subject to any disclaimer, the term of this patent is extended or adjusted under 35 U.S.C. 154(b) by 401 days.

(21) Appl. No.: 10/876,322

(22) Filed: Jun. 24, 2004

(65) Prior Publication Data

US 2005/0288445 A1 Dec. 29, 2005

(51) Int. Cl.
*G07F 1/361* (2006.01)

(52) U.S. Cl. .............. 252/582; 204/157.5; 204/157.7; 549/474; 558/303

(58) Field of Classification Search ........... 549/474; 252/582; 204/157.5, 157.7; 558/303
See application file for complete search history.

(56) References Cited

U.S. PATENT DOCUMENTS

| | | | |
|---|---|---|---|
| 6,067,186 A | 5/2000 | Dalton et al. | |
| 6,348,992 B1 | 2/2002 | Zhang et al. | |
| 6,361,717 B1 | 3/2002 | Dalton et al. | |
| 6,514,434 B1 | 2/2003 | He et al. | |
| 6,616,865 B1 | 9/2003 | Zhang et al. | |
| 6,716,995 B2 | 4/2004 | Huang et al. | |
| 6,750,603 B2 | 6/2004 | Huang et al. | |
| 2002/0084446 A1 | 7/2002 | Dalton et al. | |
| 2002/0160282 A1 | 10/2002 | Huang et al. | |
| 2003/0107027 A1 | 6/2003 | Huang et al. | |
| 2003/0146420 A1 | 8/2003 | Do et al. | |
| 2003/0201713 A1 | 10/2003 | Huang et al. | |
| 2003/0205701 A1 | 11/2003 | Huang et al. | |
| 2004/0065869 A1 | 4/2004 | Do et al. | |
| 2004/0065870 A1 | 4/2004 | Do et al. | |

FOREIGN PATENT DOCUMENTS

| WO | WO 01/79750 A1 | 10/2001 |
|---|---|---|
| WO | WO 02/08215 A1 | 1/2002 |
| WO | WO 02/14305 A2 | 2/2002 |

OTHER PUBLICATIONS

Dalton, Larry R. et al., "From molecules to opto-chips: organic electro-optic materials," J. Mater. Chem., 1999, 9, 1905-1920.

He, Mingqian et al., "Synthesis of Chromophores with Extremely High Electro-optic Activity. 1. Thiophene-Bridge-Based Chromophores," Chem. Mater. 2002, 14, 4662-4668.

Zhang, Cheng et al., "Electric Poling and Relaxation of Thermoset Polyurethane Second-Order Nonlinear Optical Materials: Role of Cross-Linking and Monomer Rigidity," Macromolecules 2001, 34, 235-243.

*Primary Examiner*—Zinna N. Davis
(74) *Attorney, Agent, or Firm*—Knobbe Martens Olson & Bear LLP

(57) ABSTRACT

A reverse synthetic strategy for making organic non-linear optical chromophores involves building up the chromophore from the electron-withdrawing end toward the electron-donating end.

8 Claims, 7 Drawing Sheets

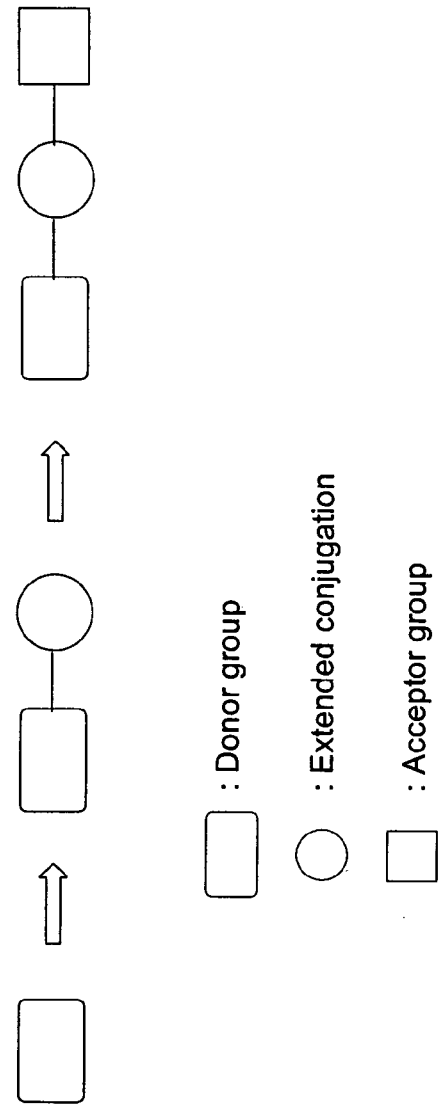
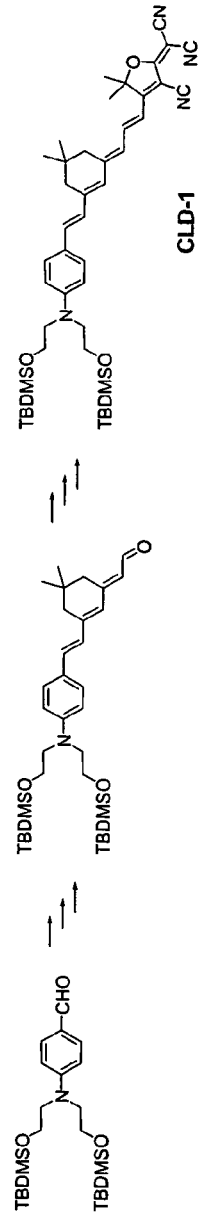
FIGURE 3A
Conventional Synthetic Strategy (Prior Art):
: Donor group
: Extended conjugation
: Acceptor group
FIGURE 3B

FIGURE 5A

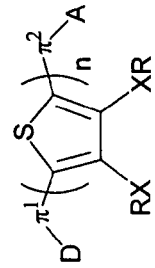

I

D is an electron donating group having low electron affinity relative to the electron affinity of A A is an electron accepting group having high electron affinity relative to the electron affinity of D $\pi^1$ is absent or a bridge that provides electronic conjugation between D and the remainder of the molecule $\pi^2$ is absent or a bridge that provides electronic conjugation between A and the remainder of the molecule $R^1$ is halogen, alkyl, aryl, or heteroalkyl $R^2$ is hydrogen, halogen, alkyl, aryl, or heteroalkyl n = 0 or 1

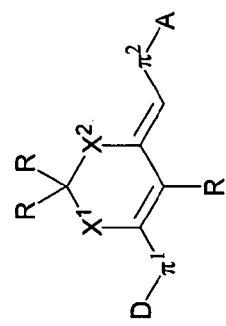

II

D is an electron donating group having low electron affinity relative to the electron affinity of A A is an electron accepting group having high electron affinity relative to the electron affinity of D $\pi^1$ is absent or a bridge that provides electronic conjugation between D and the remainder of the molecule $\pi^2$ is absent or a bridge that provides electronic conjugation between A and the remainder of the molecule R is hydrogen, alkyl, aryl, or heteroalkyl $X^1$ is O or S $X^2$ is O, S, a single bond, or $CR_2$

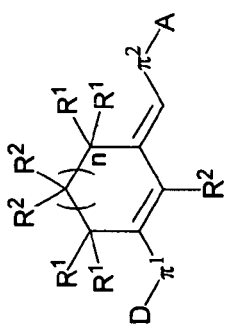

III

D is an electron donating group having low electron affinity relative to the electron affinity of A A is an electron accepting group having high electron affinity relative to the electron affinity of D $\pi^1$ is absent or a bridge that provides electronic conjugation between D and the remainder of the molecule $\pi^2$ is absent or a bridge that provides electronic conjugation between A and the remainder of the molecule R is alkyl, aryl, or heteroalkyl X is O or S n = 1-4

Donors:

Acceptors:

Conjugated bridges:

R = alkyl, aryl, or heteroaryl;  R¹ = hydrogen, alkyl, aryl, or heteroaryl;  X = O, S, Se, or Te;  Y = O, S, or Se;
Z = O, S, Se, or NR;  m = 1 or 2;  n = 1 or 2.

REVERSE SYNTHETIC METHODS FOR MAKING ORGANIC NON-LINEAR OPTICAL MATERIALS

BACKGROUND OF THE INVENTION

1. Field of the Invention

This invention relates to a general synthetic method for making organic non-linear optical materials which are useful in various applications such as in the fabrication of electro-optic devices.

2. Description of the Related Art

Electro-optic materials contain highly polarizable electrons. When an electric field is applied to these materials, the electron polarization changes significantly, resulting in an increase in index of refraction and a decrease in the velocity of the light passing through the materials. This electric field-dependent index of refraction change can be configured to perform a variety of functions such as transduction of electrical signals to optical signals, optical switching, millimeter wave signal generation, optical beam steering, radio-frequency detection, microwave-frequency detection, millimeter wave-frequency detection, phase control, power splitting, and wavelength division multiplexing (WDM). Devices that utilize electro-optic materials can be used in a wide variety of applications, e.g., signal transduction for cable television (CATV), broadband internet access, full scale holographic projection, gyroscopes for missile guidance, etc.

A number of inorganic and organic electro-optic materials are known. Organic electro-optic materials typically contain an organic non-linear optical chromophore that is dispersed or attached to a polymeric matrix. The chemical structures of some typical organic non-linear optical chromophores are shown in FIG. 1. As illustrated in FIG. 2, organic non-linear optical chromophores generally have one or more electron-withdrawing groups at one end and one or more electron-donating groups at the other, linked together by extended conjugation. The conventional synthetic strategy for preparing organic non-linear optical chromophores has been to build the chromophore from the electron-donating end, step by step, toward the electron-withdrawing end as illustrated in FIGS. 3A and 3B. Although hundreds of organic non-linear optical chromophores have been prepared using the conventional synthetic strategy, in many cases the syntheses have numerous steps, in some cases leading to lower yields and higher overall costs. Hence, the conventional synthetic strategy for preparing organic non-linear optical chromophores is not entirely satisfactory.

SUMMARY OF THE INVENTION

A reverse synthetic strategy for preparing organic non-linear optical chromophores has now been invented. In preferred embodiments, this reverse synthetic strategy involves building up the chromophore from the electron-withdrawing end toward the electron-donating end as illustrated in FIGS. 4A and 4B.

A preferred embodiment provides a method for making a non-linear optical chromophore, comprising: reacting an electron-withdrawing nucleophilic compound with an extended conjugation compound to form an electron-withdrawing extended conjugation compound; reacting the electron-withdrawing extended conjugation compound with a base to form a nucleophilic electron-withdrawing extended conjugation compound; and reacting the nucleophilic electron-withdrawing extended conjugation compound with an electron-donating compound to thereby form a non-linear optical chromophore, a non-linear optical chromophore comprising an electron-withdrawing group, extended conjugation, and an electron-donating group.

These and other embodiments are described in greater detail below.

BRIEF DESCRIPTION OF THE DRAWINGS

These and other aspects of the invention will be readily apparent from the following description and from the appended drawings (not to scale), which are meant to illustrate and not to limit the invention, and wherein:

FIG. 3A schematically illustrates the conventional synthetic strategy for preparing non-linear optical chromophores. FIG. 3B illustrates the conventional synthetic strategy for preparing CLD-1.

DETAILED DESCRIPTION OF THE PREFERRED EMBODIMENTS

Figure 1:
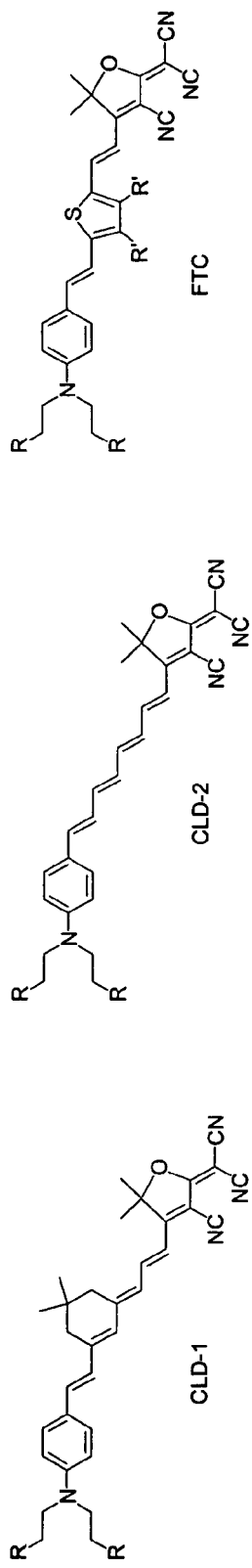
FIG. 1 shows the chemical structures of typical organic non-linear optical chromophores known as CLD-1, CLD-2, and FTC.
Figure 2:
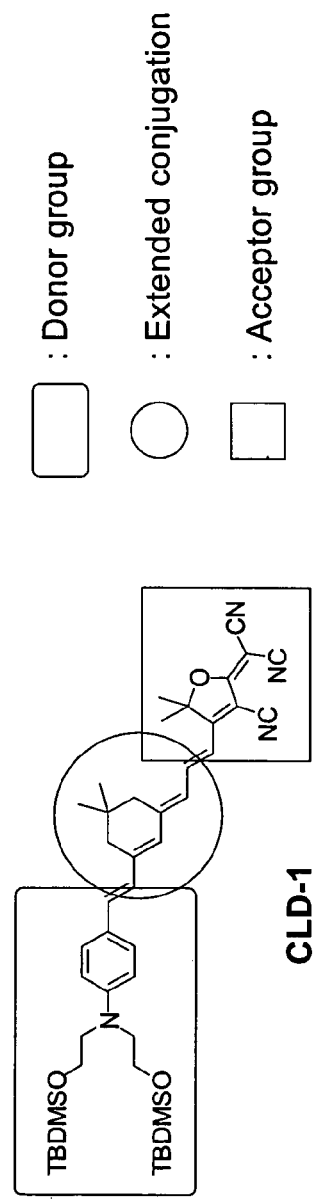
FIG. 2 schematically illustrates the electron withdrawing ("acceptor") electron-donating ("donor") and extended conjugation parts of a typical organic non-linear optical chromophore.

As illustrated in FIG. 2, a non-linear optical chromophore such as the illustrated CLD-1 can be considered to have three parts: (1) a donor group at one end of the chromophore, (2) an acceptor group at the other end, and (3) extended conjugation linking the donor group to the acceptor group. The donor group typically contains one or more electron-donating groups such as the TBDMSO-substituted dialkylamino group shown in the donor group of CLD-1. The acceptor group typically contains one or more electron-withdrawing groups such as the cyano groups shown in the acceptor group of CLD-1, and the extended conjugation typically contains one or more pi-bonded chemical groups such as the multiple carbon-carbon double bonds shown in the extended conjugation of CLD-1.

A donor group is an atom or group of atoms that has a low oxidation potential, so that the atom or group of atoms can donate electrons to an acceptor "A" through a pi-bridge. Typically, a donor group contains at least one heteroatom that has a lone pair of electrons capable of being in conjugation with the p-orbitals of an atom directly attached to the heteroatom such that a resonance structure can be drawn that moves the lone pair of electrons into a bond with the p-orbital of the atom directly attached to the heteroatom to formally increase the multiplicity of the bond between the heteroatom and the atom directly attached to the heteroatom so that the heteroatom gains formal positive charge. Exemplary donor groups include but are not limited to $R_2N—$ and RX, where R is alkyl, aryl, or heteroaryl, and where X is O, S, Se, or Te.

An acceptor group is an atom or group of atoms that has a low reduction potential, such that the atom or group of atoms can accept electrons from a donor group through a pi-bridge. Typically, an acceptor group contains at least one electronegative heteroatom that is part of a pi-bond (a double or triple bond) such that a resonance structure can be drawn that moves an electron pair of the pi-bond to the heteroatom and concomitantly decreases the multiplicity of the pi-bond so that the heteroatom gains formal negative charge.

Extended conjugation, also referred to as a pi-bridge or as a conjugated bridge, comprises an atom or group of atoms through which electrons can be delocalized from an electron donor to an electron acceptor through the orbitals of atoms in the bridge. Typically, the orbitals will be p-orbitals on double ($sp^2$) or triple (sp) bonded carbon atoms such as those found in alkenes, alkynes, neutral or charged aromatic rings, and neutral or charged heteroaromatic ring systems.

Figure 5B:
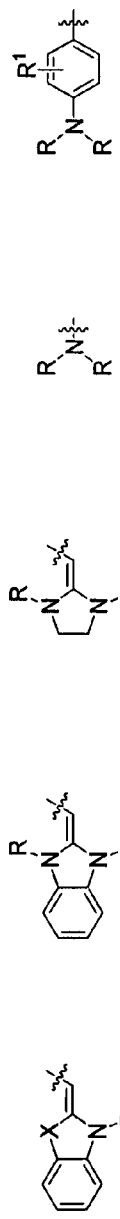
FIG. 5A illustrates the chemical structures for preferred non-linear optical chromophores having formulas I, II, and III. Preferred chemical structures for the "D" (donor), "A" (acceptor) and "π" (conjugated bridge) units are shown in FIG. 5B.
Figure 5B:
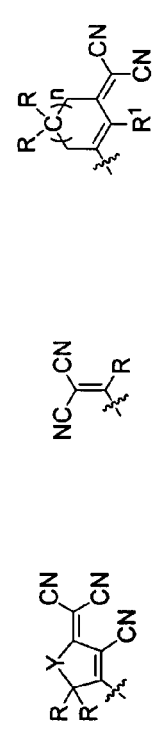
Figure 5B:

FIG. 5A illustrates examples of preferred chemical structures for non-linear optical chromophores having formulas I, II, and III. Examples of preferred chemical structures for the donor, acceptor and conjugated bridges are shown in FIG. 5B.

Figure 4A:
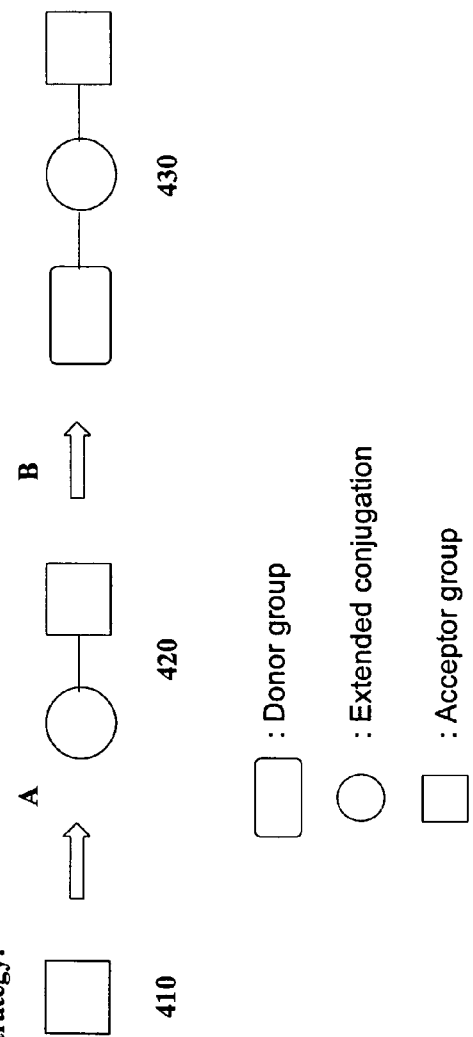
FIG. 4A schematically illustrates a preferred reverse synthetic strategy for preparing non-linear optical chromophores.
Figure 4B:
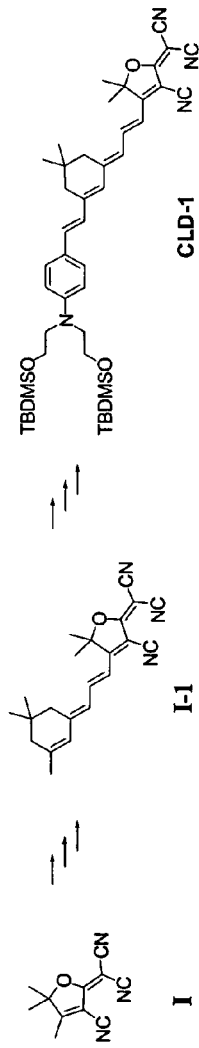
FIG. 4B illustrates a preferred reverse synthetic strategy for preparing CLD-1.

FIG. 4A schematically illustrates a preferred synthetic strategy for making a non-linear optical chromophore that involves building up the chromophore from the acceptor group end toward the donor group end. Preferably, the overall synthesis utilizes one or more nucleophilic substitution reactions. In the illustrated embodiment, the acceptor group 410 is preferably an electron-withdrawing nucleophilic compound that reacts with an extended conjugation compound by a nucleophilic substitution reaction A to form an electron-withdrawing extended conjugation compound 420. For example, FIG. 4B illustrates the reaction of electron-withdrawing nucleophilic compound I with an extended conjugation compound to form the electron-withdrawing extended conjugation compound I-1. Preferably, the acceptor group 410 bears one or more electron-withdrawing groups (such as the cyano groups of compound I) that facilitate the nucleophilic substitution reaction A by increasing the nucleophilicity of the acceptor group 410. Those skilled in the art will understand that the illustrated nucleophilic substitution reaction A may represent one or more individual chemical reactions, not all of which are necessarily nucleophilic substitution reactions. Thus, the electron-withdrawing extended conjugation compound 420 may be formed in one step or in several steps from the electron-withdrawing nucleophilic compound 410, as desired.

Preferably, another nucleophilic substitution reaction B is used to form a non-linear optical chromophore 430 by reacting the electron-withdrawing extended conjugation compound 420 with a donor group as illustrated in FIG. 4A. Those skilled in the art will understand that the nucleophilic substitution reaction B is facilitated by the electron withdrawing groups on the acceptor group 410. The attachment of the donor group to the end of the electron-withdrawing extended conjugation compound 420 that is generally opposite to the electron withdrawing groups on the acceptor group 410 is facilitated by the extended conjugation. Thus, as illustrated in FIG. 4B, the electron-withdrawing effect of the cyano groups on the electron-withdrawing extended conjugation compound I-1 is transmitted to the opposite end of the molecule by the extended conjugation, thereby facilitating a nucleophilic substitution with the donor group (bearing an electron-donating TBDMSO-substituted dialkylamino group) to form CLD-1. As discussed above with respect to reaction A, those skilled in the art will understand that the illustrated nucleophilic substitution reaction B may represent one or more individual chemical reactions, not all of which are necessarily nucleophilic substitution reactions. Thus, the non-linear optical chromophore 430 may be formed in one step or in several steps from the electron-withdrawing extended conjugation compound 420, as desired.

The non-linear optical chromophore 430 comprises one or more electron-withdrawing groups, extended conjugation, and one or more electron-donating groups. Preferred electron withdrawing groups include nitro, cyano, $C_1$-$C_3$ nitroalkyl, $C_1$-$C_3$ cyanoalkyl, $C_2$-$C_{10}$ unsaturated nitroalkyl, $C_2$-$C_{10}$ unsaturated cyanoalkyl, $C_6$-$C_{10}$ nitroaryl, $C_6$-$C_{10}$ cyanoaryl, $C_2$-$C_{10}$ nitro-heteroaryl, and $C_2$-$C_{10}$ cyano-heteroaryl. Preferably, one or more of the electron-withdrawing groups are present on the acceptor group 410 that is used to prepare the non-linear optical chromophore 430, thereby facilitating nucleophilic substitution as discussed above. The extended conjugation portion of the non-linear optical chromophore 430 preferably comprises one or more pi-bonded chemical groups. Examples of suitable pi-bonded chemical groups include carbon-carbon double bonds, carbon-carbon triple bonds, and aromatic rings.

The extended conjugation portion of the non-linear optical chromophore 430 is preferably built up in one or more chemical reactions, preferably nucleophilic substitution reactions stabilized by the presence of electron-withdrawing group(s) on the acceptor group 410. The extended conjugation compound and/or the electron-donating compound used to form the non-linear optical chromophore 430 preferably comprises a carbon-carbon double bond and/or a synthon for a carbon-carbon double bond. More preferably, the extended conjugation compound and/or the electron-donating compound comprise a carbon-oxygen double bond, e.g., an aldehyde or ketone group that is capable of undergoing a nucleophilic substitution reaction to form a carbon-carbon double bond.

Figure 6A:
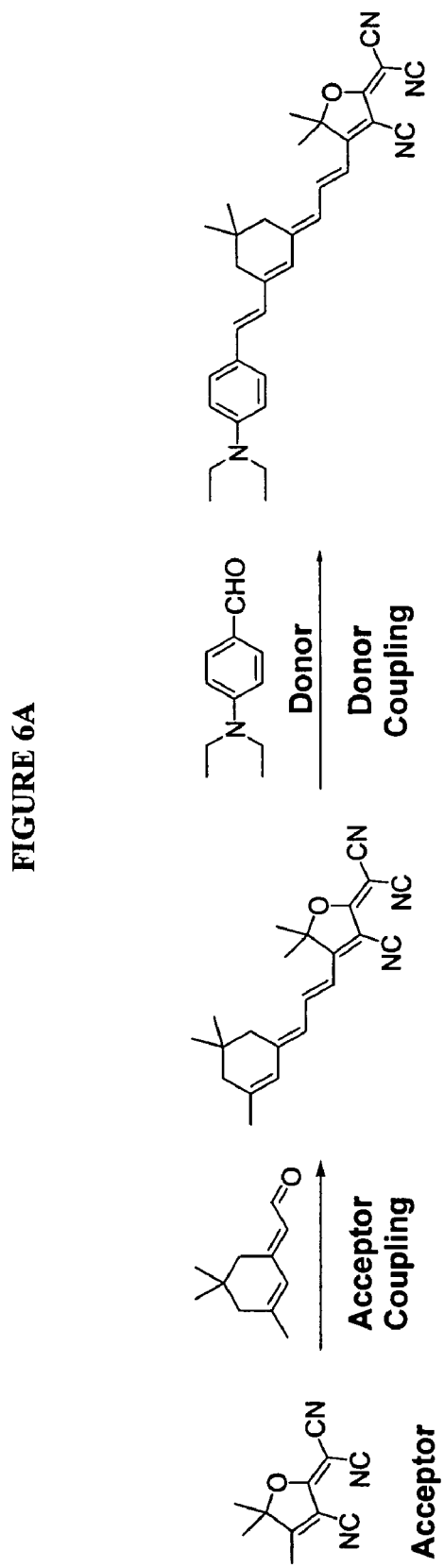
FIG. 6A summarizes a preferred synthetic scheme for making a non-linear optical chromophore.
Figure 6B:
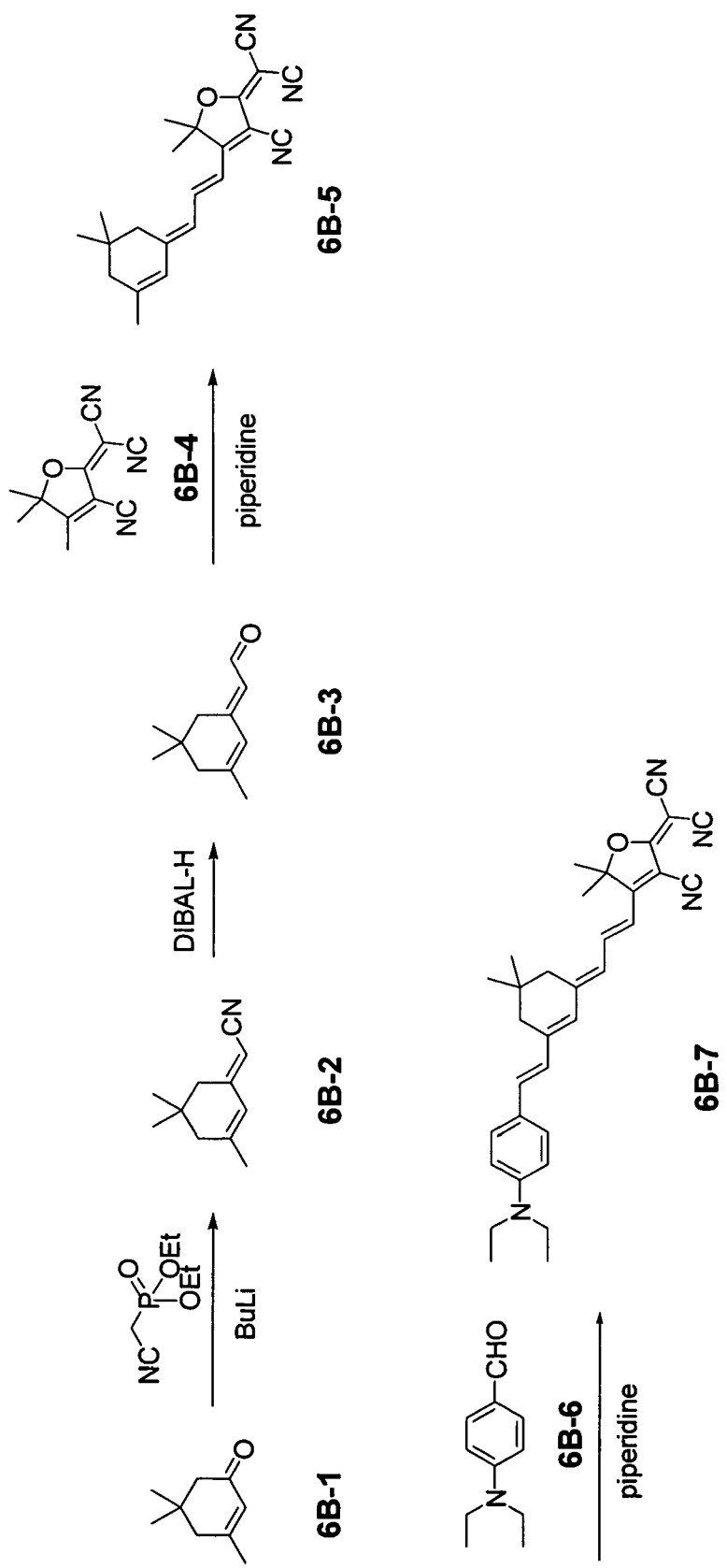
FIG. 6B illustrates in greater detail the preferred synthetic scheme summarized in FIG. 6A.

An example of a preferred synthetic scheme for making a non-linear optical chromophore is summarized in FIG. 6A and illustrated in greater detail in FIG. 6B. As summarized in FIG. 6A, this synthetic scheme involves two basic steps, an "acceptor coupling" step and a "donor coupling" step. In this context, the term "acceptor coupling" or "π bridge and/or acceptor coupling" refers to the synthetic chemical step or steps that comprise reacting an electron-withdrawing nucleophilic compound with an extended conjugation compound to form an electron-withdrawing extended conjugation compound. Typically, the coupling involves either reacting a π-bridge or acceptor group containing a carbonyl with a selected chemical structure containing at least one acidic proton, or reacting a π-bridge or acceptor group containing at least one acid proton with a selected chemical structure containing a reactive carbonyl group. The reaction is typically carried out under basic condition where the acidic proton is deprotonated and becomes a nucleophilic agent that attacks the reactive carbonyl group. The term "donor coupling" or "π bridge and/or donor coupling" refers to the synthetic chemical step or steps that comprise reacting the electron-withdrawing extended conjugation compound with a base to form a nucleophilic electron-withdrawing extended conjugation compound; and reacting the resulting nucleophilic electron-withdrawing extended conjugation compound with an electron-donating compound to thereby form a non-linear optical chromophore. Typically, the coupling involves either reacting a π-bridge or donor group containing a carbonyl with a selected chemical structure containing at least one acidic proton, or reacting a π-bridge or donor group containing at least one acid proton with a selected chemical structure containing a reactive carbonyl group. The reaction is typically carried out under basic condition where the acidic proton is deprotonated and becomes a nucleophilic agent that attacks the reactive carbonyl group. FIG. 6B illustrates in greater detail the preferred synthetic scheme summarized in FIG. 6A.

In a preferred embodiment, the method for making a non-linear optical material described above further comprises forming a non-linear optical composition, the non-linear optical composition comprising the non-linear optical chromophore and a polymer. Preferably, the polymer is an amorphous polymer having good thermal, chemical and photochemical stability, and a glass transition temperature well above the temperature at which it is expected to operate. More preferably, the optical loss of the polymer at telecommunication wavelengths (e.g., 1.3 µm and 1.55 µm) is as low as possible, and the glass-transition temperature of the polymer is about 100° C. or higher. Non-limiting examples of preferred classes of polymers include poly(acrylate), poly(carbonate), poly(imide), poly(urethane) and poly(quinoline). Poly(methyl methacrylate) is an example of a preferred poly(acrylate). The polymer may be crosslinked or non-crosslinked, as desired.

The non-linear optical composition comprising the non-linear optical chromophore and a polymer may be formed by a variety of techniques generally known to those skilled in the art such as by mechanical mixing and copolymerization, and thus the non-linear optical chromophore may be dispersed and/or attached to the polymer, as desired. For example, mechanical mixing of the non-linear optical chromophore and the polymer may be conducted in bulk by, e.g., intermixing the melted components at an elevated temperature, or in solution by e.g., dissolving the components in a common solvent. Preferably, mechanical mixing is conducted with sufficient stirring to evenly disperse the non-linear optical chromophore throughout the polymer. Mixing may also be carried out by covalently attaching the non-linear optical chromophore to the polymer. Such covalent attachment may be carried out by copolymerizing a monomeric form of the non-linear optical chromophore with the monomer components of the polymer, and/or by reacting a suitably functionalized non-linear optical chromophore with a polymer.

EXAMPLE

The synthesis illustrated in FIG. 6B is conducted as follows:

Synthesis of 6B-2

A three-necked round-bottomed flask of suitable size is equipped with a Teflon-coated magnetic stirrer and a dropping funnel. The complete setup is flame-dried using a Bunsen burner, while continuously flushed with dry nitrogen, using two needles through septa as inlet and outlet for the gas stream. The nitrogen flow is continued during the complete reaction until aqueous work up. The flask is loaded with a mixture of 13.3 g (1.55 equiv.) of dry diethyl (cyanomethyl)phosphonate and approximately 100 mL dry tetrahydrofuran (THF). The solution is cooled to −78° C., and via a syringe, 1.5 equiv of 1.6 M butyllithium in hexanes is slowly added and the mixture is stirred for 15 min. At this temperature, 6.9 g (1.0 equiv) of dry isophorone 6B-1 in 20 mL of dry THF is added via the dropping funnel. The mixture is allowed to warm to room temperature and stirred for 2 hours. To quench anions, a saturated ammonium chloride solution is added, and the aqueous and organic layers are separated in a separatory funnel. The aqueous layer is extracted three times with diethyl ether, and subsequently the organic layers are combined and washed with a saturated sodium chloride solution. The organic layer is dried over magnesium sulfate, and after filtration of the solids, the crude product is concentrated in vacuo. Removal of excess phosphono compound is effected with a silica gel flash column using diethyl ether/petroleum ether (1:1 v/v) as eluent. The product 6B-2 is collected after removing solvent in vacuo.

Synthesis of 6B-3

A three necked round-bottomed flask of suitable size is equipped with a Teflon-coated magnetic stirrer. The complete setup is flame-dried using a Bunsen burner, while continuously flushing with dry nitrogen, using two needles through septa as inlet and outlet for the gas stream. The nitrogen flow is continued during the complete reaction until aqueous workup. The flask is loaded with a mixture of 3.2 g (1.0 equiv) of 6B-2 and approximately 100 mL of dry toluene. The solution is cooled to −50° C. Via a syringe, 2.5 equiv of 1.0 M diisobutyl aluminum hydride (DIBALH) in toluene is slowly added. The mixture is stirred for 30 minutes at −50° C. Subsequently 1.75 g of silica gel slurry (100 g of $SiO_2$ and 37.5 mL of distilled water), for each milliliter of DIBALH used, is added. The thick slurry is stirred at room temperature for 2 hours. To absorb the water content, magnesium sulfate is added. The solids are filtered off and thoroughly rinsed with diethyl ether. The filtrate is concentrated in vacuo, and the product is purified using silica gel column chromatography, using diethyl ether/petroleum ether (1:4 v/v) as eluent. The product 6B-3 is collected after removing solvent in vacuo.

Synthesis of 6B-5

A round-bottomed flask equipped with a Teflon-coated magnetic stirrer is loaded with a mixture of 3.3 g (1.0 equiv) of 6B-3, 4.0 g (1.0 equiv) of 6B-4 and approximately 50 mL of chloroform. Three drops of piperidine are added at room temperature, and the resulting solution is stirred at room temperature for 3 h. After condensation, the product is purified using silica gel column chromatography, using ethyl acetate/hexane (1:4 v/v) as eluent. The product 6B-5 is isolated after removing solvent in vacuo.

Synthesis of 6B-7

A round-bottomed flask equipped with a Teflon-coated magnetic stirrer is charged with a mixture of 3.4 g (1.0 equiv) of 6B-5, 1.8 g (1.0 equiv) of 6B-6 and approximately 50 mL of chloroform. Three drops of piperidine are added at room temperature, and the resulting solution is heated to reflux for 4 hours. After cooling to room temperature and condensation, the product is purified using silica gel column chromatography, using ethyl acetate/hexane (1:4 v/v) as eluent. The product 6B-7 is isolated after removing solvent in vacuo.

All literature references and patents mentioned herein are hereby incorporated by reference in their entireties. Although the foregoing invention has been described in terms of certain preferred embodiments, other embodiments will become apparent to those of ordinary skill in the art in view of the disclosure herein. Accordingly, the scope of the present invention is not limited by the recitation of preferred embodiments.

What is claimed is:

1. A method for making a non-linear optical material, comprising:

reacting an electron-withdrawing nucleophilic compound with an extended conjugation compound to form an electron-withdrawing extended conjugation compound;

reacting the electron-withdrawing extended conjugation compound with a base to form a nucleophilic electron-withdrawing extended conjugation compound; and reacting the nucleophilic electron-withdrawing extended conjugation compound with an electron-donating compound to thereby form a non-linear optical chromophore, the non-linear optical chromophore comprising an electron-withdrawing group, extended conjugation, and an electron-donating group.

2. The method of claim 1 in which the electron-withdrawing group is selected from the group consisting of nitro, cyano, $C_1$-$C_3$ nitroalkyl, $C_1$-$C_3$ cyanoalkyl, $C_2$-$C_{10}$ unsaturated nitroalkyl, $C_2$-$C_{10}$ unsaturated cyanoalkyl, $C_6$-$C_{10}$ nitroaryl, $C_6$-$C_{10}$ cyanoaryl, $C_3$-$C_{10}$ nitro-heteroaryl, and $C_3$-$C_{10}$ cyano-heteroaryl.

3. The method of claim 1 in which the electron-donating group is —$R^1$—$NR^2R^3$, wherein $R^1$ is selected from the group consisting of $C_1$-$C_3$ alkyl, $C_2$-$C_{10}$ unsaturated alkyl, $C_6$-$C_{10}$ aryl, and $C_3$-$C_{10}$ heteroaryl; and wherein $R^2$ and $R^3$ are each individually selected from the group consisting of hydrogen, optionally substituted $C_1$-$C_{10}$ alkyl, optionally substituted $C_6$-$C_{10}$ aryl, and optionally substituted $C_3$-$C_{10}$ heteroaryl.

4. The method of claim 1, wherein the extended conjugation of the non-linear optical chromophore is situated between the electron withdrawing group and the electron donating group and comprises a carbon-carbon double bond.

5. The method of claim 1, wherein the extended conjugation of the non-linear optical chromophore is situated between the electron withdrawing group and the electron donating group and comprises an aromatic ring.

6. The method of claim 1, wherein the extended conjugation of the non-linear optical chromophore is situated between the electron withdrawing group and the electron donating group and comprises a carbon-carbon triple bond.

7. The method of claim 1 in which the electron-donating compound comprises a carbon-oxygen double bond.

8. The method of claim 1, wherein the extended conjugation compound of the non-linear optical chromophore is situated between the electron withdrawing group and the electron donating group and comprises a carbon-oxygen double bond.

* * * * *